United States Patent [19]

Stemmann

[11] Patent Number: 5,636,990
[45] Date of Patent: Jun. 10, 1997

[54] DEVICE FOR SECURING AN INSERT ON AN IMPLANT

[76] Inventor: Hartmut Stemmann, Kollaustrasse 6, D-22529 Hamburg, Germany

[21] Appl. No.: 401,196

[22] Filed: Mar. 9, 1995

[30] Foreign Application Priority Data

Mar. 15, 1994 [DE] Germany ............. 44 08 781.0

[51] Int. Cl.⁶ .................................................. A61C 13/235
[52] U.S. Cl. ........................... 433/189; 433/173; 433/141
[58] Field of Search ............................. 433/173, 174, 433/175, 176, 189, 141; 81/125

[56] References Cited

U.S. PATENT DOCUMENTS

| | | | |
|---|---|---|---|
| 2,750,828 | 6/1956 | Wendling | 81/125 |
| 3,007,504 | 11/1961 | Clark | 81/125 |
| 3,690,005 | 9/1972 | Edelman | 433/176 |
| 4,824,371 | 4/1989 | Deutsch et al. | 433/189 |
| 4,997,372 | 3/1991 | Shiner et al. | 433/189 |
| 5,462,436 | 10/1995 | Beaty | 433/141 |

FOREIGN PATENT DOCUMENTS

| | | |
|---|---|---|
| 3739434A1 | 5/1988 | Germany. |
| 9207951.2 | 1/1993 | Germany. |
| 9306146.3 | 9/1993 | Germany. |
| 4328779A1 | 3/1994 | Germany. |

OTHER PUBLICATIONS

"Magnetverankerungen auf Implantaten," Jakob; Jäger, Kurt; Schmidli, Fredy; *Quintessenz* 44, 891–898 (1993).

*Primary Examiner*—Cary E. O'Connor
*Attorney, Agent, or Firm*—Austin R. Miller

[57] ABSTRACT

In implantation surgery, in order for an insert, which surrounds a magnetic cell or a ferromagnetic part in a gastight manner, to be secured reliably and firmly, flattened areas are provided distributed about the circumference of the insert in such a way that sections having the full wall thickness of the insert sleeve remain between the flattened areas. For engagement with the insert, an applicator element is provided which has an engagement section for positive engagement with the flattened areas on the insert, and a magnetic cell or a ferromagnetic part which ensures a nonpositive engagement between insert and applicator element.

8 Claims, 2 Drawing Sheets

DEVICE FOR SECURING AN INSERT ON AN IMPLANT

The invention relates to a device for securing an insert on an implant. The device is intended for implantation surgery in and on the head, the skull, face, mouth and throat areas, when an insert is to be secured on an implant.

As a consequence of the surgical procedures involved in implantations, the operating field is covered in blood and is wet, and this makes it very difficult to see clearly when fitting an insert. The invention is therefore based on the object of making available a device by means of which inserts can be secured reliably and very firmly on an implant.

According to the invention, this is essentially achieved by virtue of the fact that, in the case of a cylindrical insert in whose shell a magnetic cell or a ferromagnetic part is enclosed in a gastight manner, flattened areas are provided distributed about the circumference of the insert in such a way that sections having the full wall thickness of the insert shell remain between the flattened areas. An applicator element can be brought into positive engagement with this insert, the said element having an engagement section, which is shaped corresponding to the flattened areas, and a magnetic cell or a ferromagnetic part which ensures a nonpositive connection between insert and applicator element.

In this way an insert can be screwed reliably and very firmly into an implant. As a result of the magnetic hold, it is not possible for the insert, which is generally very small, to fall out of the applicator element, even under the effect of jerking movements, and possibly be inhaled in the ease where the insert is being fitted in the throat area. As soon as the insert has been placed safely on the implant head, it can be screwed in firmly, for example with a known surgical ratchet screwdriver.

BRIEF DESCRIPTION OF THE DRAWINGS

Illustrative embodiments of the invention are discussed in greater detail below, with reference to the drawing, in which.

DETAILED DESCRIPTION OF THE INVENTION

Figure 1:
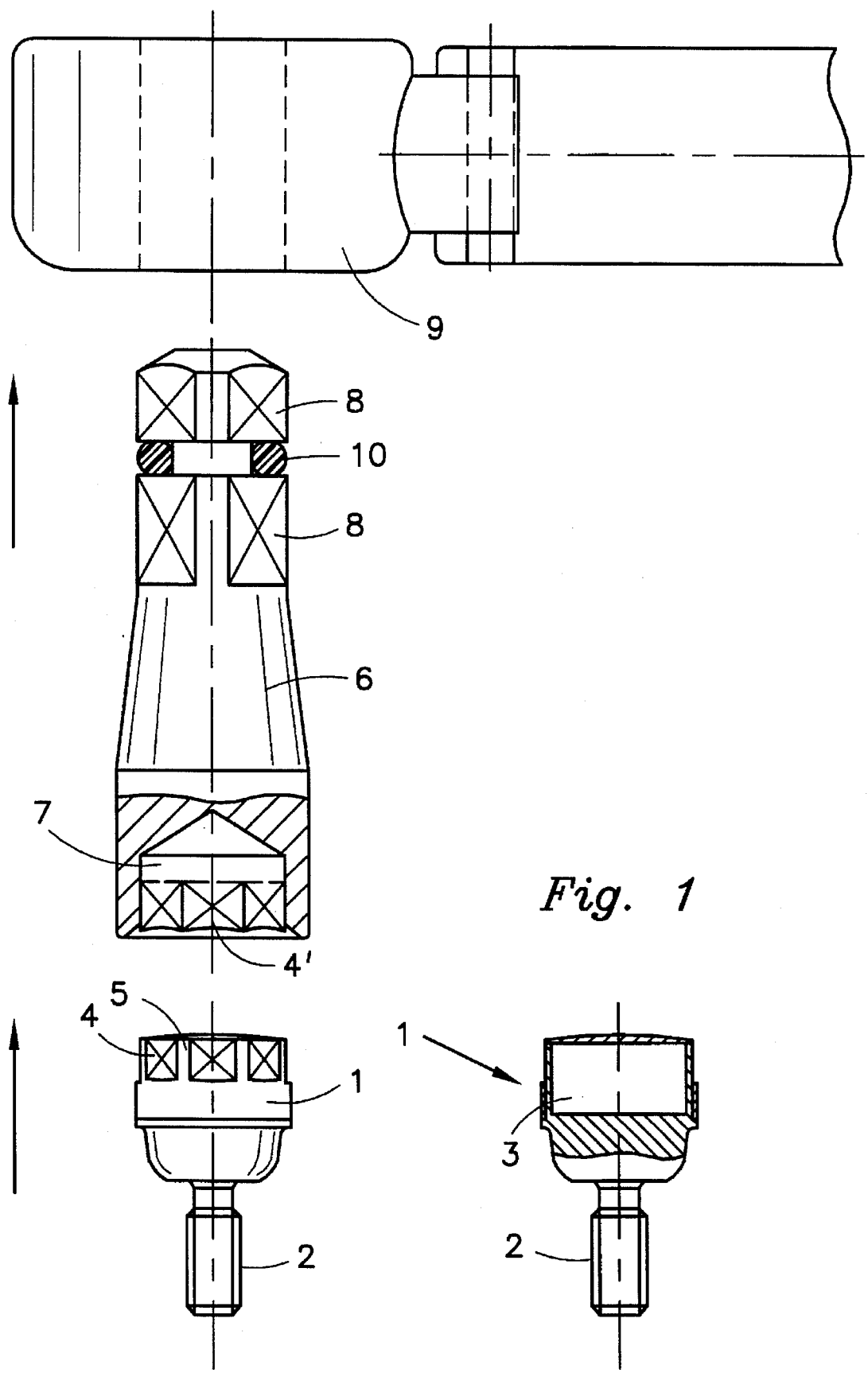
FIG. 1 shows an applicator element with insert.

In FIG. 1 an insert is labelled 1, this insert being provided with a threaded shank 2 by means of which the insert is screwed into an implant or an implant head (not shown). On the underside the insert 1 is cup-shaped, the lower edge being rounded or bevelled starting from a plane bottom surface. Arranged on the cup-shaped lower part is a cylindrical section in which a magnetic cell 3 is arranged. The magnetic cell 3 is surrounded by a thin shell of the insert, which shell may in parts be only 0.05 mm thick and consists of pure titanium. On the outer periphery of the upper edge of this cylindrical section, the insert 1 is provided, in this illustrative embodiment, with a total of eight flattened areas 4, these being spaced apart from one another so that a narrow section 5 of the original outer surface of the otherwise cylindrical shell of the insert remains. At these narrow sections 5, the shell of the insert exhibits its original wall thickness, whereas at the flattened areas 4 the wall thickness is reduced.

Column-shaped sections of full wall thickness are formed by the sections 5 between the flattened areas 4, which column-shaped sections ensure that the masticatory pressure on the insert 1 is taken up without the insert being deformed. These column-shaped sections 5 also ensure that when the insert is screwed into the implant, during which a torque of up to 30 Ncm is applied by means of a ratchet screwdriver, the shell of the insert is not deformed. When screwing the insert firmly in the implant, the insert is screwed down tight so that the gap between the plane bottom surface of the insert and the correspondingly plane top of the implant is closed as snugly as possible in order to prevent bacteria from penetrating into the thread area.

The magnetic cell 3 is welded into the insert 1 in a gastight manner, for example by laser welding, in order to prevent corrosion of the magnetic cell, since magnetic alloys, as well as ferromagnetic alloys, are very susceptible to corrosion. In the event of deformation of the insert sleeve, hairline cracks could appear and these would trigger the corrosion process, with the result that the products of corrosion would penetrate in ionized form into the tissue, for example into the gingiva and bone. The titanium implant would be wasted as a result of this.

An approximately cylindrical applicator element is labelled 6 and has, at its lower end face, a recess 7 on whose inner periphery there are flattened areas 4' corresponding to the flattened areas 4 on the insert 1. In this case the flattened areas 4' can directly adjoin one another and can be designed correspondingly wider than the flattened areas 4 on the insert, the individual flattened area 4' being continued as far as the line of intersection with the adjacent flattened area. However, the fit between the engagement section of the insert 1 and of the applicator element 6 must be accurate to a hundredth of a millimeter in order to achieve a good positive locking between the two engagement sections. The applicator element 6 is provided at the upper end with four flattened areas 8 on the outer circumference, these flattened areas serving as engagement surfaces for a socket spanner or a torque-controlled ratchet screwdriver 9. In the illustrative embodiment shown, the flattened areas 8 are divided by an annular groove in which an O-ring 10 is arranged, which protrudes slightly outwards in the region of the flattened areas 8 and serves for a better fitting of the tool 9 on the engagement section of the applicator element 6. A magnet or a part made of a ferromagnetic alloy is enclosed in the applicator element 6, as is described with reference to FIG. 2.

Figure 2:
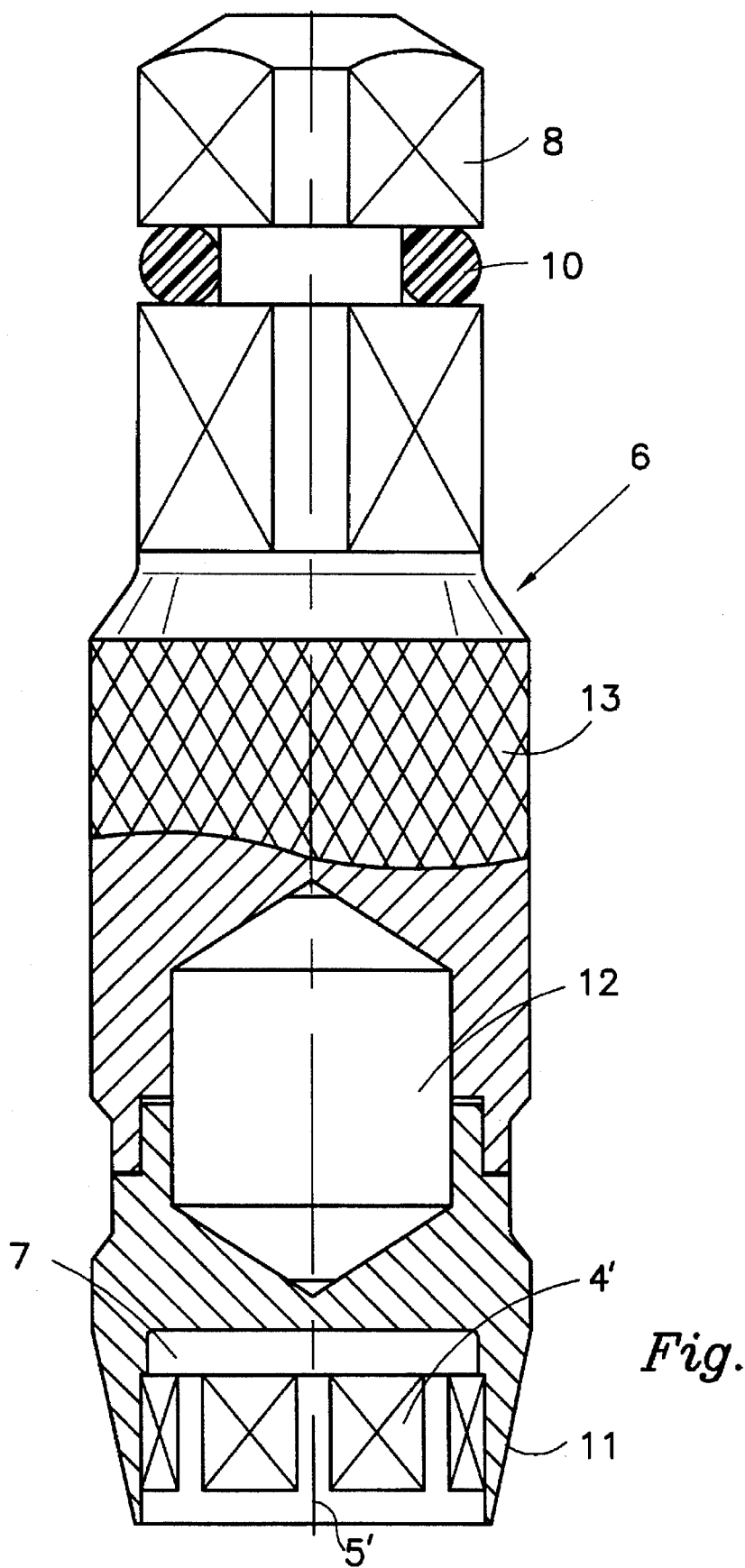
FIG. 2 shows another embodiment of the applicator element, partly in cross-section.

FIG. 2 shows, partly in cross-section, another embodiment of the applicator element 6, where the lower edge 11 surrounding the recess 7 has a cross-section designed in the shape of a slender wedge running out to a narrow point, so that when the insert is being screwed in by means of the applicator element, the gingiva is gently displaced and is not traumatized. This is particularly important in the case of subcutaneous insert application. When the insert is being tightened, the end of the applicator element running out to a point can also penetrate slightly into the gap between implant and bone structure, without the applicator element being lifted during the tightening of the insert.

In this embodiment the recess 7 has a plane bottom surface which serves as a limit stop for the insert, and the flattened areas 4' are arranged spaced apart from one another such that spaces 5' are formed between them, corresponding to the design on the insert 1 in FIG. 1.

The applicator element 6 is designed in two parts in order to accommodate a ferromagnetic cell 12 which is embedded in a corrosion-proof manner, by means of laser welding, in the titanium jacket of the applicator element. The ferromagnetic cell 12 is activated as soon as an insert 1 is pushed into the recess of the applicator element. A secure magnetic connection is provided during the entire treatment procedure.

On the outer circumference of the central section 13, the applicator element 6 is provided with a knurled surface so that the insert can be screwed in reliably by hand even when there is moisture from the mouth on the applicator element.

The applicator element 6 is, like the other parts, made of pure titanium in order to prevent foreign metal contamination on the insert 1 and in the implant environment. The O-ring 10 can consist of silicone or another material permitted in the medical sector. It prevents the tool and the applicator element from slipping apart during the treatment.

Upon treatment, the insert 1 is fitted into the applicator element 6, with the flattened areas on both parts mutually engaging. The magnetic effect draws the insert with exact fitting as far as the bottom limit stop, after which the insert and applicator element can be handled as one part.

The exposed head part of the implant and the surrounding gingiva are carefully cleaned, disinfected and drained, following which the insert is screwed in by hand together with the applicator element, until it is felt to be sitting lightly on the implant head. The screwing instrument 9 is then attached to the applicator element 6, and the screwing procedure is continued until the torque lock is triggered. As soon as the insert is firmly connected to the implant, the applicator element 6 can be withdrawn simply.

In a modified embodiment, the engagement part lying above the O-ring can be connected releasably to the applicator element 6, so that different carrier elements for different tools can be arranged on the applicator element 6. In this connection, it is also possible to use a conventional apparatus for screwing in the insert by motor.

It is also possible for a depression to be formed at the upper end face of the applicator element for the engagement of a wrench for socket head screws.

A ferromagnetic alloy can be provided in the insert 1 instead of a magnetic cell, which ferromagnetic alloy is likewise welded-in in a gastight manner and interacts with a magnetic cell in the applicator element 6.

Instead of the eight flattened areas on the circumference of the insert, it is also possible for a smaller number of flattened areas to be provided. The flattened areas 4 can also be formed on a lower section of the circumference of the insert.

I claim:

1. A combination insert and applicator particularly useful for dental prosthetics, said combination comprising:

(a) an insert constructed to be secured on an implant by said applicator, said insert comprising a substantially cylindrical wall, said wall having varying thicknesses and an exterior surface, on said exterior surface having flattened areas separated by columnar areas, said wall at said columnar areas having a greater thickness than at said flattened areas, said insert further comprising a magnetic body enclosed in said insert in a gastight manner, said magnetic body being selected from the group consisting of a magnetic cell and a ferromagnetic part, and (b) an applicator having a first and a second engagement portion, said first engagement portion being constructed for positive engagement with said flattened areas on said insert and at least a part of said second engagement portion being constructed for engagement with a tool, said second engagement portion including an annular groove and an O-ring positioned in said annular groove, said applicator having enclosed therein a magnetic body selected from the group consisting of a magnetic cell and a ferromagnetic part, said magnetic body in said applicator being positioned to provide non-positive engagement with said insert when said insert is positively engaged with said first engagement portion.

2. A combination according to claim 1, said insert further comprising an upper edge adjacent to said flattened areas, said upper edge defining an applicator engagement end on said insert.

3. A combination according to claim 1, said first engagement portion further comprising a tapering edge portion, said tapering edge portion defining an insert engagement end on said first engagement portion.

4. A combination according to claim 1, wherein at least a portion of said applicator has a knurled outer surface.

5. A combination according to claim 1, wherein said second engagement portion includes an outer surface having flattened areas.

6. A combination according to claim 1, wherein said second engagement portion is constructed to be releasably engageable with said tool.

7. A combination according to claim 1, wherein said applicator is constructed from pure titanium.

8. A combination according to claim 1, wherein said magnetic body in said applicator is enclosed in a gastight manner.

* * * * *